(12) United States Patent
Kazakevich

(10) Patent No.: US 9,979,949 B2
(45) Date of Patent: May 22, 2018

(54) METHOD AND APPARATUS FOR OBTAINING STEREOSCOPIC 3D VISUALIZATION USING COMMERCIALLY AVAILABLE 2D ENDOSCOPES

(75) Inventor: Yuri Kazakevich, Newton, MA (US)

(73) Assignee: VIKING SYSTEMS, INC, Westborough, MA (US)

(*) Notice: Subject to any disclaimer, the term of this patent is extended or adjusted under 35 U.S.C. 154(b) by 703 days.

(21) Appl. No.: 13/547,510

(22) Filed: Jul. 12, 2012

(65) Prior Publication Data
US 2013/0176395 A1  Jul. 11, 2013

Related U.S. Application Data

(60) Provisional application No. 61/507,317, filed on Jul. 13, 2011.

(51) Int. Cl.
| | |
|---|---|
| H04N 13/00 | (2018.01) |
| H04N 13/02 | (2006.01) |
| A61B 1/00 | (2006.01) |
| A61B 1/04 | (2006.01) |

(52) U.S. Cl.
CPC ......... *H04N 13/02* (2013.01); *A61B 1/00193* (2013.01); *A61B 1/00195* (2013.01); *A61B 1/042* (2013.01)

(58) Field of Classification Search
CPC . A61B 1/00193; A61B 1/00195; A61B 1/042; H04N 13/00
USPC ...... 348/45, 42, 49, 46, 51, 65, 75; 600/111, 600/101
See application file for complete search history.

(56) References Cited

U.S. PATENT DOCUMENTS

| | | | |
|---|---|---|---|
| 5,612,816 A | 3/1997 | Strähle et al. | |
| 5,702,350 A | 12/1997 | Vry et al. | |
| 5,751,341 A | 5/1998 | Chaleki et al. | |
| 5,808,813 A | 9/1998 | Lucey | |
| 5,828,487 A | 10/1998 | Greening et al. | |
| 6,338,711 B1* | 1/2002 | Sekiya ............... | A61B 1/00193 348/45 |
| 7,621,868 B2 | 11/2009 | Breidenthal et al. | |
| 2011/0228049 A1* | 9/2011 | Kazakevich et al. ........... | 348/45 |

* cited by examiner

*Primary Examiner* — Michael Teitelbaum
*Assistant Examiner* — Jean W Desir
(74) *Attorney, Agent, or Firm* — Frederick J M Price; Bond, Schoeneck & King, PLLC

(57) ABSTRACT

An adapter for optically coupling a conventional 2D endoscope to a stereoscopic 3D camera so as to provide stereoscopic 3D visualization of an object imaged by the conventional 2D endoscope, the adapter comprising:
a body;
a mechanical mount disposed on the body for mechanically mounting the adapter to a conventional 2D endoscope;
means for mounting the body to a stereoscopic 3D camera; and
an optical pathway disposed within the body for receiving an image from the exit pupil of the conventional 2D endoscope and projecting the received image on an appropriate portion of the stereoscopic 3D camera, wherein the optical pathway is adjustable so as to accommodate a range of different conventional 2D endoscopes.

18 Claims, 8 Drawing Sheets

METHOD AND APPARATUS FOR OBTAINING STEREOSCOPIC 3D VISUALIZATION USING COMMERCIALLY AVAILABLE 2D ENDOSCOPES

REFERENCE TO PENDING PRIOR PATENT APPLICATION

This patent application claims benefit of pending prior U.S. Provisional Patent Application Ser. No. 61/507,317, filed Jul. 13, 2011 by Yuri Kazakevich for METHOD AND APPARATUS FOR OBTAINING STEREO 3D VISUALIZATION USING COMMERCIALLY AVAILABLE 2D ENDOSCOPES, which patent application is hereby incorporated herein by reference.

FIELD OF THE INVENTION

This invention relates to visualization devices in general, and more particularly to endoscopes.

BACKGROUND OF THE INVENTION

U.S. Pat. No. 5,702,350 to Vry et al. describes a system in which an adapter is used to connect a stereoscopic endoscope to stereoscopic electronic documentation devices (e.g., stereoscopic CCD cameras). This system utilizes a stereoscopic endoscope (or line of stereoscopic endoscopes) specifically designed as a part of the overall stereoscopic system described in the patent. As shown in the patent, the stereoscopic endoscopes have specially designed optics and specially designed mechanical connectors to match with the set of stereoscopic documentation devices (e.g., stereoscopic CCD cameras).

As opposed to the cited prior art, and as will hereinafter be discussed in detail, the present invention teaches a method and apparatus for adapting virtually any conventional, commercially-available non-stereoscopic endoscope (i.e., a 2D endoscope) to a fixed stereo camera so as to obtain stereoscopic 3D visualization.

More particularly, the configuration of a typical conventional rigid non-stereoscopic endoscope is well known in the art. FIG. 1 shows the structure of the endoscope. The non-stereoscopic (i.e., 2D) endoscope 10 comprises an elongated shaft 11, a proximal housing 12, a light post 13 and an eyepiece 14. The shaft 11 typically includes at least one thin-wall inner tube 15 in addition to the outer tube 16. Illumination fiber bundle 17 extends from the light post 13 to the distal end of the endoscope and typically is sandwiched between the inner tube 15 and the outer tube 16. The inner tube 15 carries the optical train that typically comprises an objective lens 18, and a number of rod-lens optical relay systems 19a, 19b, . . . , 19n. Some endoscopes feature an oblique direction of view (e.g., 30° with respect to the longitudinal axis of the shaft 11), typically achieved by a prism 20. A negative lens 21 is disposed at the distal tip of the endoscope for expansion of the optical field of view and is hermetically sealed to the shaft 11. Sometimes an additional plane window is used at the distal tip of the endoscope for sealing the assembly, instead of using the negative lens 21 for both optical and sealing purposes. The objective lens 18 creates the first intermediate image 22 of an object under observation. Each relay system 19 creates a next intermediate image, thereby carrying the image of the object through the narrow shaft from the distal end of the endoscope 10 to the proximal end of the endoscope 10. The last intermediate image is created at the proximal end of the endoscope 10.

FIG. 2 shows the detail of a typical proximal end construction of the 2D endoscope 10. The last optical intermediate image 22n is created behind the last optical relay system 19n. At the location of the image 22n, a field stop 23 is disposed that delineates the designed optical field of view and removes stray light. Typically, the field stop 23 is constructed as a thin diaphragm with a round opening in its center. An ocular lens 24 is disposed proximal to the field stop 23 at such a distance that the field stop 23 locates in the vicinity of the first focal plane of the ocular lens 24. On account of this construction, the ocular lens 24 creates a virtual magnified image of the field stop 23 and of the intermediate image 22n at a long distance (typically from 250 mm to infinity) from the ocular lens 24. This image may be observed by direct viewing through the eyepiece 14. The optical beam emerging from the ocular lens 24 may be considered collimated. A window 25 is disposed proximal to the ocular lens 24 and is hermetically sealed to the proximal housing 12. Thus, the 2D endoscope 10 represents a single hermetically sealed sterilizable assembly that may not be disassembled by the user. The eyepiece 14 is affixed to the proximal housing 12 and is typically made out of chemically resistant plastic, e.g., PEEK. Typically the shape and dimensions of the eyepiece are in compliance with the German standard DIN 58105. FIG. 3 shows the DIN 58105 specifications.

It is well known in the art that eyepieces formed in compliance with DIN 58105 have become the industry standard, and all major manufacturers of endoscopes produce products compatible with this eyepiece standard. When the endoscopes are used in conjunction with endoscopic cameras, the common shape of the eyepieces from different manufacturers (i.e., all complying with the DIN 58105 standard) allows for connection of different endoscopes to different cameras all across the industry. In other words, eyepieces complying with the DIN 58105 standard have become an industry standard interface for commercially available 2D endoscopes. The eyepiece is typically releasably attached to the endoscopic camera head with a locking mechanism that allows for rotation of the endoscope around its mechanical axis. Conventional endoscopes per the above description constitute the majority of commercially available endoscopes and may be found in various catalogs of endoscope manufacturers. Just a few examples are given below:

(1) Laparoscope 5 mm×30°, Part Number 26046BA by Karl Storz;

(2) Laparoscope 10 mm×0°, Part Number A4801A by Olympus;

(3) Bariatric Laparoscope 10 mm×30°, Part Number 502-657-030 by Stryker;

(4) ENT Scope, 4 mm×30°, Part Number T4302 by Linvatec; and (5) Laparoscope 10 mm×30°, Part Number 7207945 by Smith & Nephew.

Typically the endoscope is coupled to the camera via an optical device, i.e., an adapter, also known as an endocoupler or a camera coupler. The function of this optical device (i.e., adapter) is to focus the collimated light beam coming out of the ocular lens 24 onto the image sensor of the camera. Endocouplers include focusing optics and means for focus adjustment (most often via a manually rotatable focus ring). Typically manufacturers offer a range of endocouplers having different focal lengths. The image size obtained for a given endoscope on a given image sensor will be proportional to the focal length of the endocoupler. Some manufacturers produce endocouplers with optical zoom capability. The endocoupler may represent a stand-alone, hermetically-sealed, sterilizable device whose proximal end is releasably attached to the camera head and whose distal end releasably couples to the DIN 58105 eyepiece of the endoscope, thereby allowing the endoscope to rotate. Alternatively, the endocoupler may be permanently attached to the camera head (becoming an integral part of the camera head), in which case the distal portion of the integrated camera head (i.e., the camera head plus the endocoupler) will have a releasable locking mechanism for the DIN 58105 eyepiece.

Examples of just a few of the commercial stand-alone endocouplers are given below:

(1) Endocoupler, 30 mm focal length, Part Number 7204823 by Smith & Nephew;
(2) Endocoupler, Part Number PV127S by Aesculap;
(3) Zoom endocoupler, Part Number PV126S by Aesculap; and
(4) Parfocal Zoom Coupler, (20-37 mm) by Solos Endoscopy.

Examples of a few of the commercial endocouplers which are integrated with camera heads include:

(1) Camera head with coupler, Part Number OTV-SP1H-NA-12E by Olympus; and
(2) TRICAM® Parfocal Zoom 3-Chip Camera Head, Part Number 20221030 by Karl Storz.

OBJECTS OF THE INVENTION

A primary object of the present invention is to realize an endoscopic stereoscopic 3D visualization system using conventional, commercially-available 2D endoscopes.

Another object of the present invention is to realize such a system while retaining the modular, compartmentalized structure of a conventional endoscope system (i.e., endoscope/endocoupler/camera head) already familiar to, and accepted by, users.

SUMMARY OF THE INVENTION

The present invention provides an endoscopic stereoscopic 3D visualization system using conventional, commercially-available 2D endoscopes.

And the present invention provides such a system while retaining the modular, compartmentalized structure of a conventional endoscope system (i.e., endoscope/endocoupler/camera head) already familiar to, and accepted by, users.

In one preferred form of the invention, there is provided an adapter for optically coupling a conventional 2D endoscope to a stereoscopic 3D camera so as to provide stereoscopic 3D visualization of an object imaged by the conventional 2D endoscope, the adapter comprising:
a body;
a mechanical mount disposed on the body for mechanically mounting the adapter to a conventional 2D endoscope;
means for mounting the body to a stereoscopic 3D camera; and
an optical pathway disposed within the body for receiving an image from the exit pupil of the conventional 2D endoscope and projecting the received image on an appropriate portion of the stereoscopic 3D camera, wherein the optical pathway is adjustable so as to accommodate a range of different conventional 2D endoscopes.

In another preferred form of the invention, there is provided a method for providing stereoscopic 3D visualization of an object imaged by a conventional 2D endoscope, the method comprising:
providing an adapter for optically coupling a conventional 2D endoscope to a stereoscopic 3D camera, the adapter comprising:
a body;
a mechanical mount disposed on the body for mechanically mounting the adapter to a conventional 2D endoscope;
means for mounting the body to a stereoscopic 3D camera; and
an optical pathway disposed within the body for receiving an image from the exit pupil of the conventional 2D endoscope and projecting the received image on an appropriate portion of the stereoscopic 3D camera, wherein the optical pathway is adjustable so as to accommodate a range of different conventional 2D endoscopes;
positioning the adapter between the conventional 2D endoscope and the stereoscopic 3D camera so that the adapter receives an image from the conventional 2D endoscope and projects the received image on an appropriate portion of the stereoscopic 3D camera; and
adjusting the optical pathway of the adapter so that the image received from the conventional 2D endoscope is properly projected on an appropriate portion of the stereoscopic 3D camera.

In another preferred form of the invention, there is provided apparatus for optically coupling a conventional 2D endoscope to a stereoscopic 3D camera so as to provide stereoscopic 3D visualization of an object imaged by the conventional 2D endoscope, the apparatus comprising:
a kit of adapters for disposition between a conventional 2D endoscope and a stereoscopic 3D camera, wherein each of the adapters in the kit comprises:
a body;
a mechanical mount disposed on the body for mechanically mounting the adapter to a conventional 2D endoscope;
means for mounting the body to a stereoscopic 3D camera; and
an optical pathway disposed within the body for receiving an image from the conventional 2D endoscope and projecting the received image on an appropriate portion of the stereoscopic 3D camera;
wherein each of the adapters in the kit comprises a different optical pathway so as to accommodate a different conventional 2D endoscope.

In another preferred form of the invention, there is provided a method for providing stereoscopic 3D visualization of an object imaged by a conventional 2D endoscope, the method comprising:
providing a kit of adapters for disposition between a conventional 2D endoscope and a stereoscopic 3D camera, wherein each of the adapters in the kit comprises:
a body;
a mechanical mount disposed on the body for mechanically mounting the adapter to a conventional 2D endoscope;
means for mounting the body to a stereoscopic 3D camera; and
an optical pathway disposed within the body for receiving an image from the conventional 2D endoscope and projecting the received image on an appropriate portion of the stereoscopic 3D camera;

wherein each of the adapters in the kit comprises a different optical pathway so as to accommodate a different conventional 2D endoscope;

selecting an appropriate adapter from the kit and positioning that adapter between the conventional 2D endoscope and the stereoscopic 3D camera so that the adapter receives an image from the conventional 2D endoscope and properly projects that image on a portion of the stereoscopic 3D camera.

In another preferred form of the invention, there is provided apparatus for providing stereoscopic 3D visualization of an object, the apparatus comprising:

a 2D endoscope;

a stereoscopic 3D camera; and an adapter for optically coupling the conventional 2D endoscope to the stereoscopic 3D camera, the adapter comprising:

a body;

a mechanical mount disposed on the body for mechanically mounting the adapter to the conventional 2D endoscope;

means for mounting the body to the stereoscopic 3D camera; and an optical pathway disposed within the body for receiving an image from the exit pupil of the conventional 2D endoscope and projecting the received image on an appropriate portion of the stereoscopic 3D camera, wherein the optical pathway is adjustable so as to accommodate a range of different conventional 2D endoscopes.

BRIEF DESCRIPTION OF THE DRAWINGS

These and other objects, features and advantages of the present invention will be more fully disclosed or rendered obvious by the following detailed description of the preferred embodiments of the invention, which is to be considered together with the accompanying drawings wherein like numbers refer to like parts and further wherein.

DETAILED DESCRIPTION OF THE PREFERRED EMBODIMENTS

Figure 1:
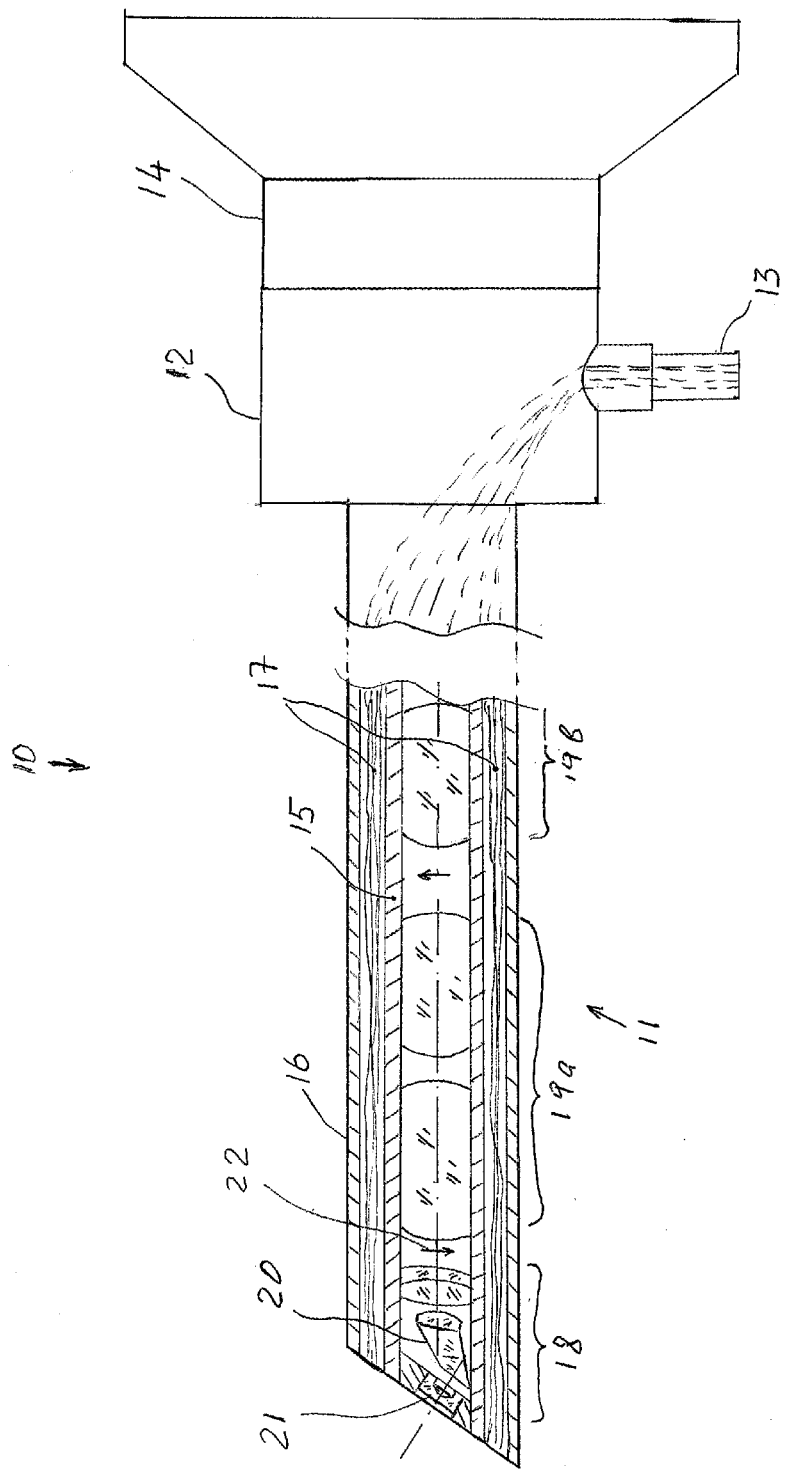
FIG. 1 is a schematic view showing a typical conventional rigid 2D endoscope.
Figure 2:
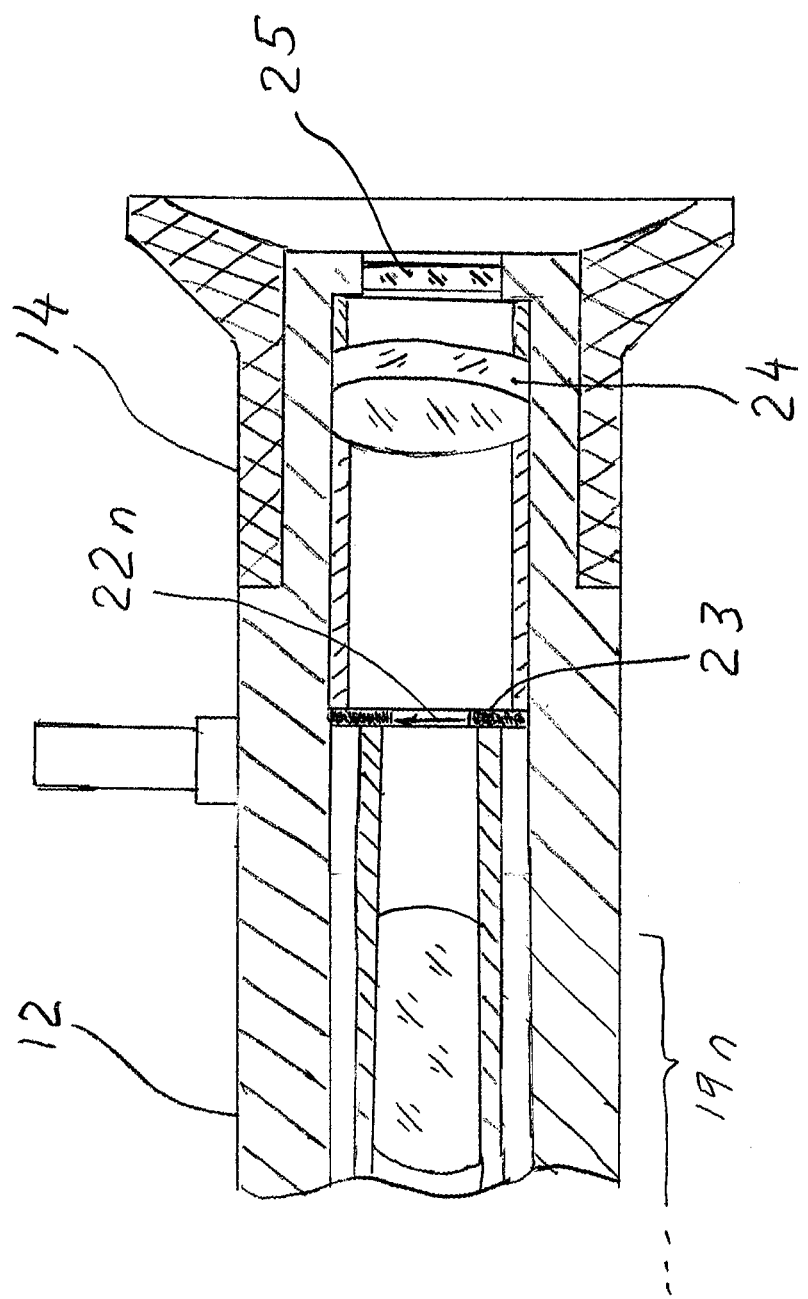
FIG. 2 is a schematic view showing the typical proximal end construction for a conventional rigid 2D endoscope.
Figure 3:
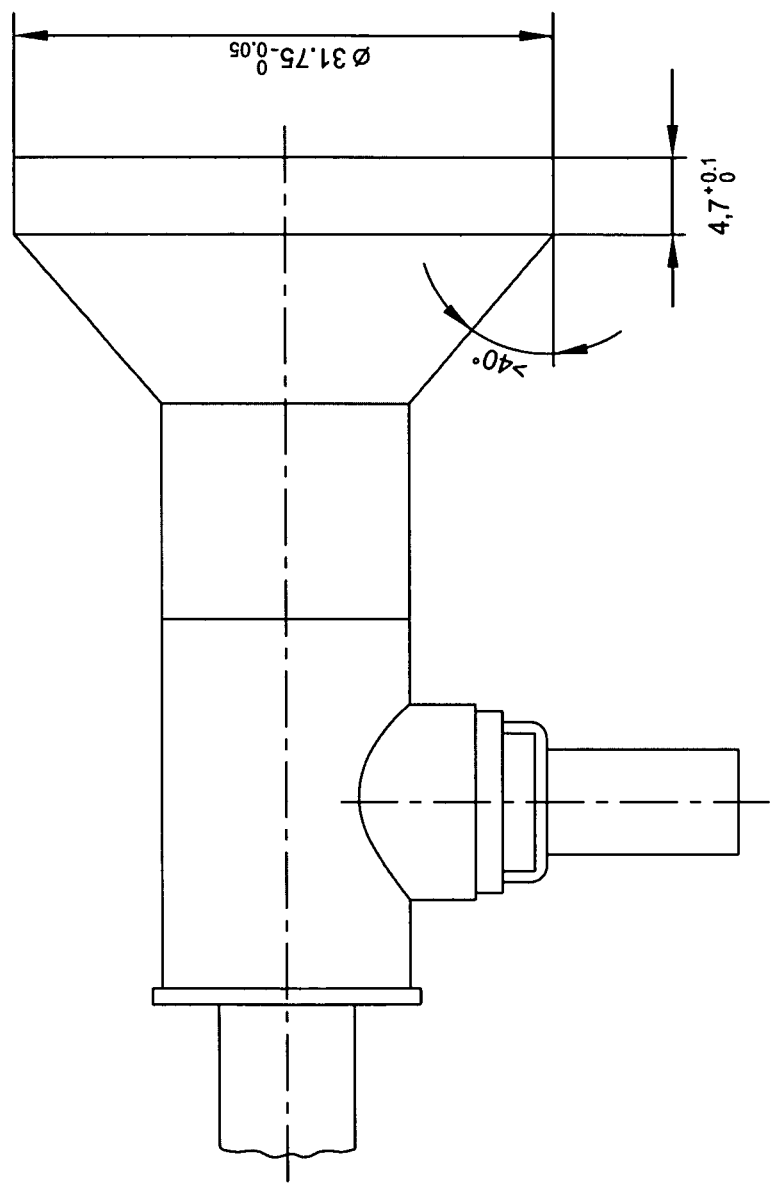
FIG. 3 is a schematic view showing the DIN 58105 specifications for an endoscope eyepiece.
Figure 4:
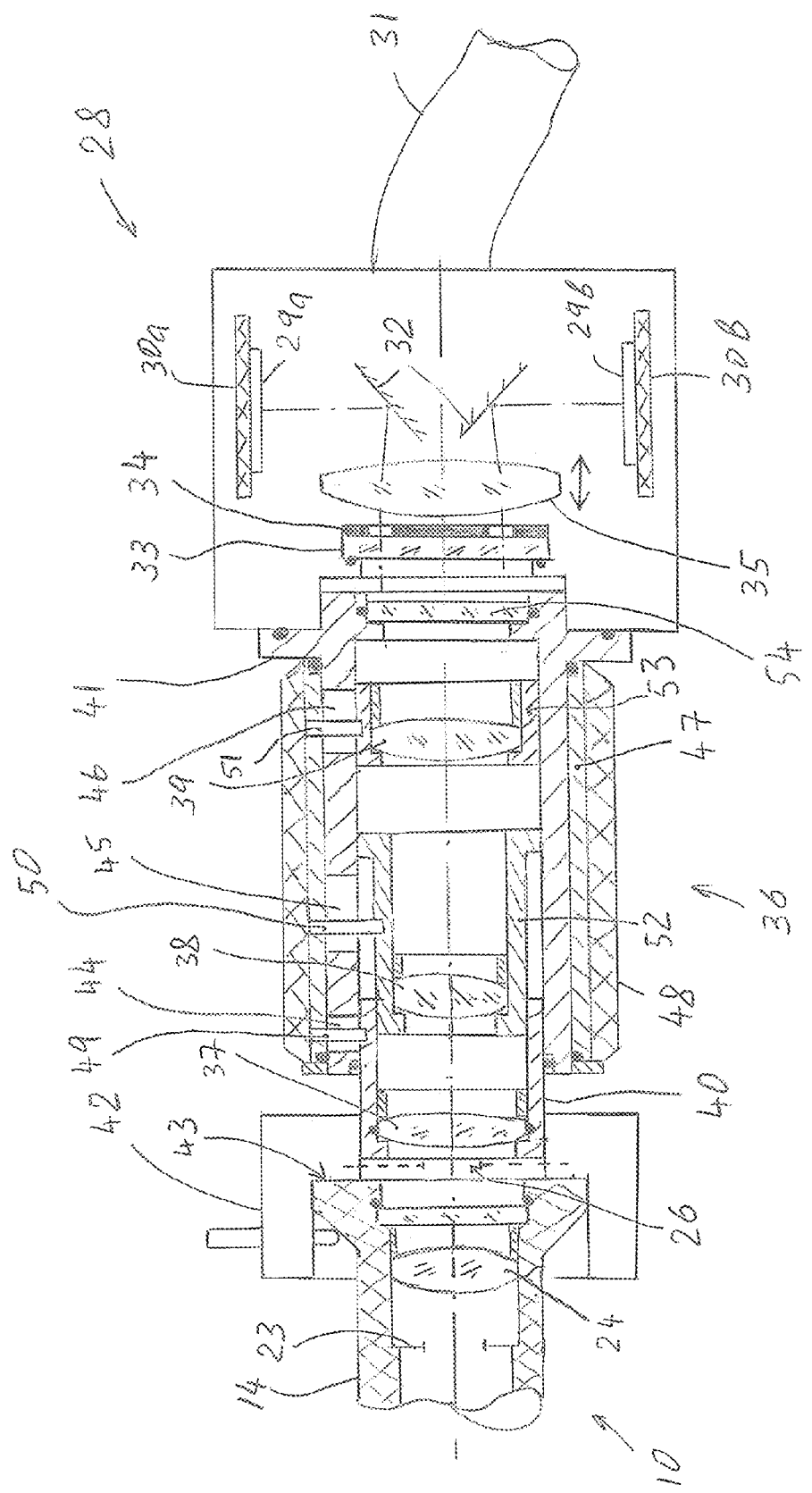
FIG. 4 is a schematic view showing an adapter for connecting a wide range of different 2D endoscopes to a stereoscopic 3D camera so as to provide stereoscopic 3D visualization.

Looking first at FIG. 4, there is shown a first embodiment of the present invention. More particularly, in this form of the invention, the system for rendering stereoscopic 3D visualization preferably includes three self-contained, hermetically-sealed components: a conventional 2D endoscope 10, a 3D adapter 36 and a 3D camera head 28. It should be appreciated that the specific optical characteristics of 2D endoscopes vary from scope to scope, based on a variety of factors, including field stop 23, ocular lens 24 and exit pupil 26. As will hereinafter be discussed, the 3D adapter must take these factors into account in order to properly provide stereoscopic visualization using a conventional 2D endoscope.

FIG. 4 shows the proximal portion of the conventional 2D endoscope 10 having the DIN 58105 eyepiece 14, the ocular lens 24 and the field stop 23. The exit pupil 26 of the endoscope is located near the second focal plane of the ocular lens 24.

The 3D camera head 28 comprises two image sensors 29a and 29b corresponding to the "Right" and "Left" images, respectively, of the 3D camera. The image sensors are typically placed on printed circuit boards 30a, 30b that contain the driver circuitry and other communication/service electronics that need to be located in physical proximity to the image sensors. The rest of the signal processing chain, as well as power supplies, etc., reside in the camera controller unit (not shown) connected to the camera head via a cable 31, as is well known in the art. The camera head 28 also includes the channel separation means 32, schematically shown in FIG. 4 by a pair of mirror surfaces. Other beam separation means are also possible, as is well known in the art. The camera head 28 receives the input optical beam from 2D endoscope 10 (and 3D adapter 36) through the entrance window 33 which is hermetically sealed to the camera head housing.

Figure 5:
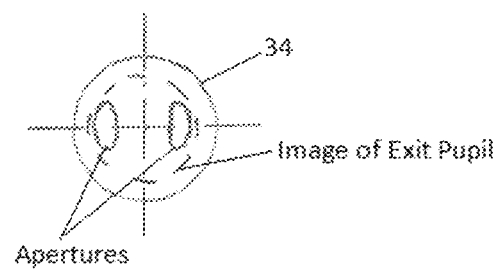
FIG. 5 is a schematic view showing a dual aperture plate of a stereoscopic 3D camera.

Proximal to the window 33 is disposed a dual aperture plate 34, which shown in more detail in FIG. 5. Dual aperture plate 34 divides the single image channel emerging from the conventional 2D endoscope 10 (and 3D adapter 36) into the two image channels forwarded to left and right image sensors 29a, 29b, respectively, of the 3D camera head 28, whereby to produce stereoscopic 3D visualization from a conventional 2D endoscope. Focusing optics 35 are schematically shown in FIG. 4 as a single lens disposed proximal to the dual aperture plate 34.

Typically the camera head is the most expensive component of the system, so the main idea behind the present invention is to create a modular system where the user would have to buy one 3D camera head and adapt most (or all) of the conventional, commercially-available 2D endoscopes (that are in a healthcare facility's inventory) to 3D visualization. This purpose is attained by providing the 3D adapter 36 which is described in more detail below. Significantly, in this form of the invention, a single 3D adapter is capable of working with a wide range of different 2D endoscopes, each having different optical characteristics, and still provide proper stereoscopic 3D visualization with a single 3D camera head 28.

In this form of the invention, the 3D adapter 36 represents a telescopic system that projects the exit pupil 26 of the endoscope 10 onto the dual aperture plate 34 of camera head 28 with appropriate magnification so that both apertures of dual aperture plate 34 are within the diameter of the projected pupil (see FIG. 5). It is well known in the art that the exit pupil sizes of conventional, commercially-available 2D endoscopes vary depending on specific designs/manufacturers, as well as based on the physical size of the endoscopes and their clinical applications. Typically smaller diameter endoscopes (e.g., arthroscopes, ENT scopes, etc.) have smaller exit pupils compared to larger diameter endoscopes (e.g., laparoscopes, thoracoscopes, etc.). In order to be able to use a single 3D camera head with various endoscopes, there should be an optical means that performs at least two functions: (1) projects the image of the exit pupil of the endoscope onto the aperture plate 34, maintaining approximately the same size of this image for different types of endoscopes; and (2) projects the image of the field stop 23 onto the image sensors 29a, 29b. The 3D adapter 36 of the present invention performs both of these functions.

Figure 6:
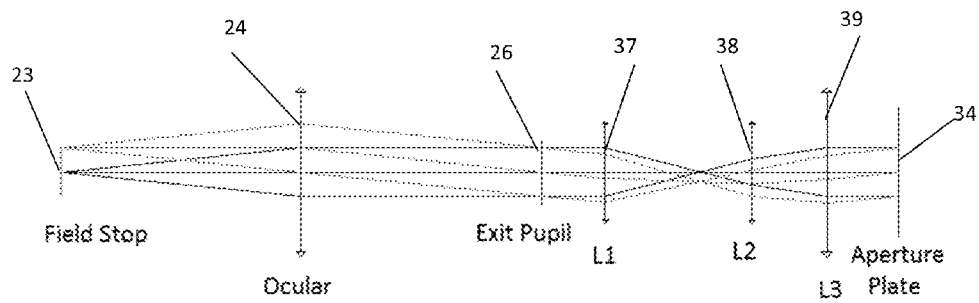
FIG. 6 is a schematic view showing a three-lens group variable focus system which may be used in connection with a relatively large exit pupil of 3 mm (typical for a laparoscope)

Mechanically, the distal end of the adapter should be able to couple to the DIN 58105 eyepiece of the conventional 2D endoscope 10, whereas the proximal end of the adapter should couple to the 3D camera head 28. FIG. 4 shows one version of such a 3D adapter. FIG. 6 shows an example of the first order optical lay-out of the system. The system in FIG. 6 represents a three-lens group variable focus system. In the lay-out, each lens group is schematically shown as a single lens. It should be appreciated that the optical system shown in FIG. 6 is not a "true zoom" system, in the sense that the total distance between the locations of the object (i.e., the exit pupil 26 of the endoscope) and the image (i.e., the aperture plate 34) does not remain the same during magnification change, as it would in a "true zoom" system. A true zoom optical system is also possible for realization of this invention if desired. Typically the true zoom system would require more lens groups and at least one group with the negative optical power. However the system shown in FIGS. 4 and 6 is simpler and uses only three lens groups, all of them having positive power. The main reason why the true zoom system is not required for the present invention is due to the fact that the exit pupil of the endoscope has to be magnified to the certain image size only once for the particular scope being used, and thereafter the position of the system can be fixed for this particular type of endoscope and not changed any more during the procedure. In other words, the physical distance between the endoscope 10 and the camera head 28 needs to be fixed during the procedure, although it does not need to be the same for different endoscopes. This principle of operation of the 3D adapter will be explained in more detail below.

The optical system of the 3D adapter is shown in FIG. 6. The three lens groups are designated as L1, L2 and L3 and also by the numerals 37, 38, 39. The optical system operates as follows.

Let's assume that the 2D endoscope 10 which is to be mounted to the 3D camera has an exit pupil 26 that requires that it be magnified by a magnification factor $M_1$ for proper use with the 3D camera. For this particular endoscope, the lenses L1, L2, and L3 shall assume specific axial positions relative to each other, and to the aperture plate 34, in order to provide the desired image magnification. These positions can be recorded as a set of distances d1, d2, d3 of each lens from the aperture plate 34. Let's now assume that a different type of endoscope 10 is used with a different exit pupil size that requires a different magnification $M_2$ for the image of the exit pupil on dual aperture plate 34 to stay unchanged. To achieve this new magnification, the lenses L1, L2 and L3 shall be disposed at different distances from the aperture plate 34. A numerical example of first-order optics design of the variable focus system is given below in Table I.

FIG. 6 shows a first-order optical lay-out corresponding to an endoscope with a relatively large exit pupil of 3 mm, which is typical for a laparoscope. The lens data for this example are assumed to be as follows:

Field stop diameter: 3 mm
Ocular focal length: 15 mm
Exit Pupil diameter: 3 mm
Distance from exit pupil to lens L1: 4 mm
Focal length of L1: 6 mm
Focal length of L2: 8 mm
Focal length of L3: 10 mm In this case, the required magnification between the exit pupil 26 and the image of the exit pupil on the dual aperture plate 34 is set to −1 for this particular example. The minus sign indicates the inverted image.

Figure 7:
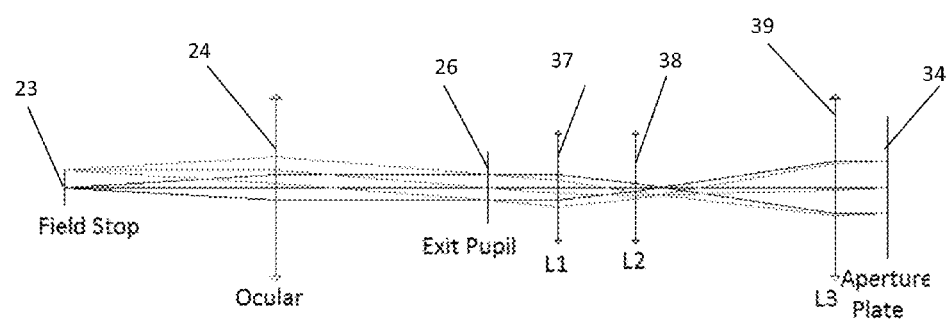
FIG. 7 is a schematic view like that of FIG. 6, except showing a system which may be used in connection with a smaller exit pupil of 1.5 mm (typical for an arthroscope)

FIG. 7 shows the lay-out corresponding to a smaller exit pupil of 1.5 mm, typical for smaller endoscopes, e.g., arthroscopes. In order to maintain the same diameter of the image of the exit pupil 26 on the dual aperture plate 34, the magnification should double to −2. As can be seen in FIG. 7, this is accomplished by different positions of lenses L1, L2 and L3. Note that in FIG. 7, the field stop diameter of the endoscope is changed to 2 mm, as would be typical of a smaller endoscope, and the ocular focal length is changed to 12 mm, again typical for smaller endoscopes. The other initial parameters remain the same as in FIG. 6.

Thus the example shows a system with magnification variability of 2 times.

All magnification values between −1 and −2 can also be attained: the positions of the lenses for the entire range, with 0.1 magnification step, is given in Table 1.

TABLE 1

| Pupil Magnification vs. L1, L2 and L3 axial positions | | | |
|---|---|---|---|
| d1 | d2 | d3 | M |
| 18.367 | 9.167 | 4.5 | −1 |
| 18.769 | 10.049 | 4.17 | −1.1 |
| 19.009 | 10.769 | 3.88 | −1.2 |
| 19.134 | 11.374 | 3.63 | −1.3 |
| 19.176 | 11.896 | 3.42 | −1.4 |
| 19.161 | 12.361 | 3.25 | −1.5 |
| 19.107 | 12.787 | 3.12 | −1.6 |
| 19.027 | 13.187 | 3.03 | −1.7 |
| 18.933 | 13.573 | 2.98 | −1.8 |
| 18.832 | 13.952 | 2.97 | −1.9 |
| 18.733 | 14.333 | 3 | −2 |

Figure 8:
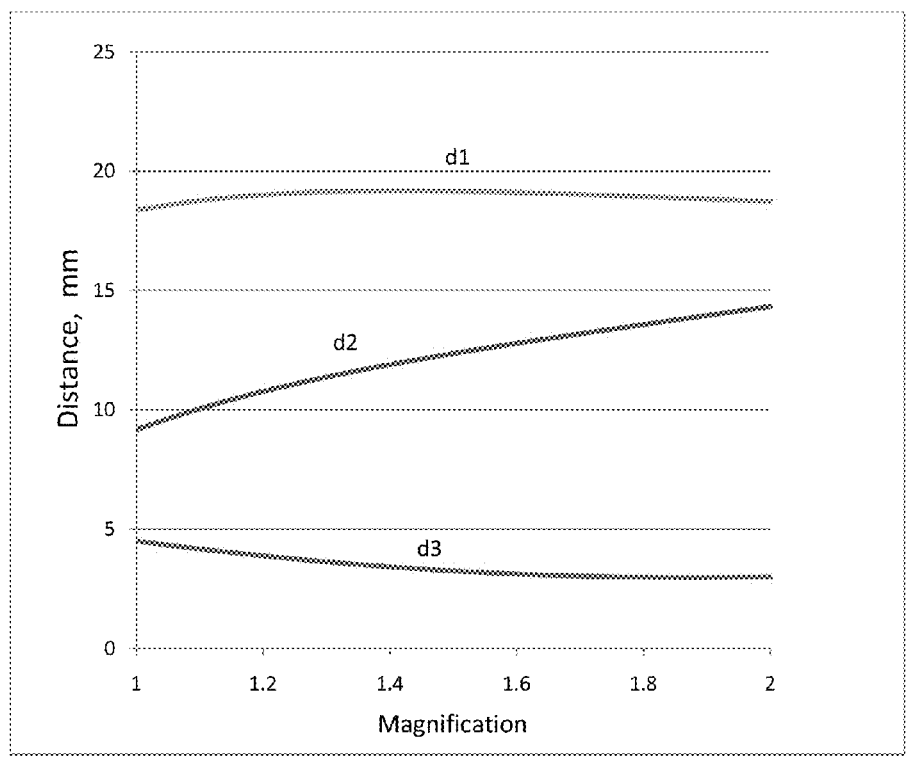
FIG. 8 is a schematic view illustrating positions of the lenses and resulting magnification.

The diagram illustrating positions of the lenses and resulting magnification (negative sign omitted) is shown in FIG. 8.

As follows from the above discussion and the given example, the system is not a "true zoom" since the distance between the endoscope 10 (or its field stop 23 as a reference) is not preserved during magnification change. Rather, the distance between the exit pupil and lens L1 remains constant. Mechanically this means that each endoscope 10 is mounted into the 3D adapter 36 in such a way that its exit pupil is disposed at a pre-determined distance from the lens L1 (4 mm in the numerical example above). Then, when magnification changes, the endoscope 10 is allowed to travel together with the lens L1 without changing the distance between L1 and the exit pupil 26.

Referring back to FIG. 4, such a mechanical arrangement is shown. Such an arrangement may be achieved by having the lens L1 mounted in a telescopic sleeve 40 that is dynamically sealed to the main housing 41 of the 3D adapter 36. The 3D adapter 36 further comprises a locking mechanism 42 that receives the DIN 58105 eyecup 14 of the conventional endoscope. Such locking mechanisms are well known in the art and are present in all of the endocoupler product examples given above. Different types and makes of endoscopes have different locations of exit pupils with respect to the proximal end 43 of the eyecup 14. However, for the proper operation of the optical system, the distance between the exit pupil 26 and the lens 37 (L1) shall be maintained constant for all the endoscopes (e.g., 4 mm as in the numerical example above). This can be easily achieved by making the locking mechanism 42 axially pre-adjustable with respect to the sleeve 40. Various known means may be used, such as a threaded connection between the housing of the locking mechanism 42 and the sleeve 40.

After the distance between the exit pupil 26 and the lens 37 has been adjusted to the designed value, the axial position of the mechanism 42 to the lens 37 is fixed, for example by means of locking screws (not shown). The axial position of the mechanism 42 to lens 37 remains fixed for the remainder of the time that the 3D adapter is used to connect that particular 2D endoscope (or that particular type of 2D endoscope) to the 3D camera. The means for axial movements of the lenses according to pre-determined relations are well known in the art and are widely used in commercially-available zoom and variable focus systems. These means are not themselves a subject of the present invention, except to the extent that they provide a means to achieve the goals of the invention, i.e., to provide stereoscopic 3D visualization using commercially available 2D endoscopes. What is shown in FIG. 4 is a simplified example of one such mechanical arrangement.

The main housing 41 of the 3D adapter 36 includes axial slots 44, 45 and 46 that maintain axial movement of the lenses 37, 38 and 39 and also limit the ranges of their axial displacements. The 3D adapter 36 also comprises a zoom sleeve 47 that includes three helical slots (not shown) designed in correspondence with the optical prescription of the zoom positions of the lenses 37, 38, 39 (such as, for example, per Table 1). The zoom sleeve 47 is permanently affixed to the adjustment ring 48. Pins 49, 50 and 51 are disposed in corresponding helical slots of the zoom sleeve 47 with the slide mechanical fit to the edges of the slots. These pins also extend through the axial slots 44, 45 and 46 where they also have a slide fit with the edges. The pins 49, 50 and 51 are affixed to the lens sleeves 40, 52 and 53, respectively. When the adjustment ring 48 is rotated by the user, the zoom sleeve 47 rotates with it, then the pins 49, 50 and 51 ride along the helical slots of the zoom sleeve 47 and simultaneously along the axial slots 44, 45, 46. The lenses 37, 38 and 39 will perform the designed axial movements, since they are being driven by the pins 49, 50 and 51 affixed to the lens sleeves 40, 52 and 53.

It should be appreciated that, for each type of commercially available 2D endoscope, the adjustment of the 3D adapter 36 is pre-set and is not intended to be changed during its actual use (e.g., during a surgical procedure). Therefore, when the 3D adapter is adjusted for a certain type of endoscope, the adjustment ring 48 may be locked by any known means, such as locking screws (not shown) so that it thereafter remains locked in that position during the use of that type of endoscope (of course, when the type of endoscope is changed, adjustment ring 48 must be unlocked and manipulated so as to adjust for the use of a different type of endoscope). In the preferred embodiment, the 3D adapter 36 represents a stand-alone, hermetically sealed, sterilizable device similar to the commercially-available 2D endocouplers used in conventional 2D endoscopic systems and the commercially-available 3D endocouplers used in conventional 3D endoscopic systems. In FIG. 4, the seals are schematically shown as O-ring cross-sections for illustration purposes only.

The proximal end of the 3D adapter 36 includes a proximal window 54 that is hermetically sealed to the housing 41. In the preferred embodiment, the 3D adapter 36 releaseably attaches to the camera head 28, e.g., by a proximally-threaded housing 41 (male thread) connecting to the female thread at the distal end of the camera head 28. Again, this connection is typical for endocouplers where a C-mount thread connection is commonly used.

It should be appreciated that FIGS. 4-8 show the general principles of one preferred construction for the present invention. Optical components schematically shown as single lenses may be compound lenses or lens groups; the details of the mechanical design may vary; the 3D adapter 36 may be permanently integrated to the camera head 28; the configuration of the apertures in the aperture plate 34 may also vary depending on the desired balance between 3D effect, light efficiency and image quality.

It should also be noted that the 3D adapter in fact constitutes an additional relay system so that the images on the image sensors 29a and 29b become inverted. The simplest way to restore the "upright" orientation of the images is by electronic means, i.e., by applying a simultaneous "mirror" and "top-to-bottom" flip to the image processing chain. These electronic means are well known in the art. Alternatively, although more cumbersome, an image-inverting prism may be included in the 3D coupler optical train.

The focusing lens 35 in the camera head 28 is schematically shown as a single lens. In practice, it may be a compound lens or a group of lenses. It can also carry a re-focusing function if combined with known means of axial movement for focusing. Moreover the lens 35 could be a zoom system that would then also adjust magnification of the image on the image sensors 29a and 29b.

The channel separation means 32 is schematically shown as two mirrors. In practice, various means are possible, such as arrangements using prisms where the image sensors 29a and 29b may be positioned in one plane perpendicular to the optical axis of the endoscope.

Thus it will be seen that, in one form of the invention, a single, adjustable 3D adapter may be interposed between any one of the many commercially available 2D endoscopes and the 3D camera, and the adjustable 3D adapter may be adjusted so as to accommodate the specific optics of the endoscope being used. In other words, in this form of he invention, a single, adjustable adapter can accommodate a wide range of different commercially available 2D endoscopes. This form of the invention can be very useful where a 3D camera must be used with a wide range of different 2D endoscopes.

There may be situations where a simplified version of the 3D adapter is advantageous. For example, if the medical facility chooses to have just one type of conventional 2D endoscope to be used for 3D visualization, a simplified 3D adapter may be used. In that case, the variable magnification feature of the 3D adapter shown in FIG. 4 is no longer necessary, and a simplified 3D adapter (having fixed magnification) may be used. Thus, in a second form of the invention, a fixed magnification 3D adapter may be provided.

Figure 9:
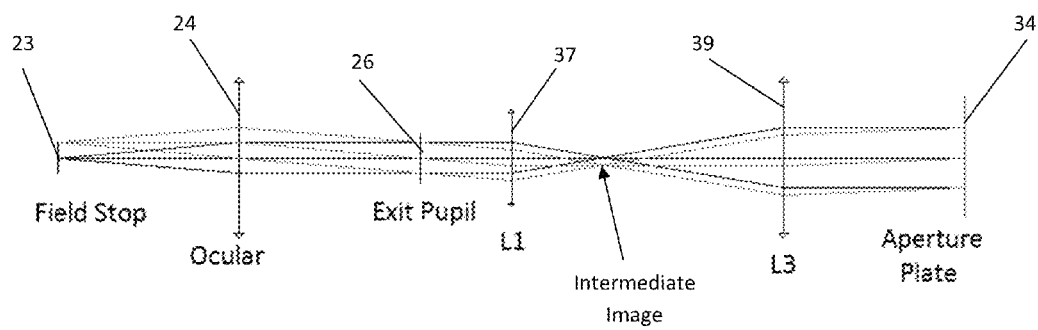
FIG. 9 is a schematic view like that of FIGS. 6 and 7, except showing a two-lens group system instead of a three-lens group system, with the lens group positions being fixed.

A simplified two-lens group optical design of the 3D adapter with fixed magnification is shown in FIG. 9 (the first-order optical design scheme is shown). In FIG. 9, the distance between the exit pupil 26 of the endoscope and the first lens L1 is equal to the focal length of L1. The intermediate image of the field stop 23 (and of the object under observation) is then formed in the vicinity of the second focal plane of the lens L1. The lens L3 is disposed at the distance from L1 that is equal to the sum of focal lengths of L1 and L3, so that the intermediate image is in the first focal plane of the lens L3. Therefore the collimated beam is obtained proximally to the lens L3. The magnification of the image of the exit pupil formed on the dual aperture plate 34 calculates as the ratio of the focal lengths of L3 and L1. The opto-mechanical implementation of this embodiment will be a significantly simplified version of the design shown in FIG. 4. There are only two lens groups instead of three lens groups. The lens group positions are fixed, so no zoom sleeves with helical slots, nor telescopic sleeves, are required.

In this form of the invention, it is possible to provide a kit of different 3D adapters, each with a different fixed magnification, with the appropriate 3D adapter being selected from the kit according to the specific optical properties of the particular 2D endoscope which is to be mounted to the 3D camera.

Figure 10:
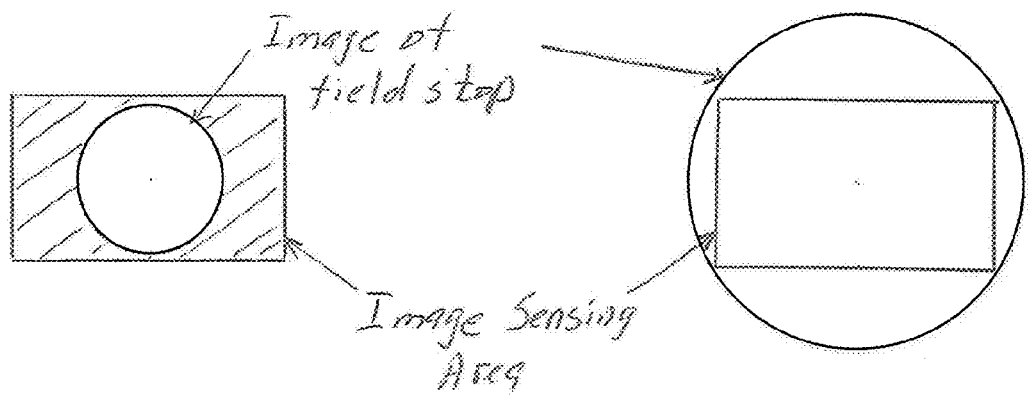
FIG. 10 is a schematic view showing various ways in which an image may be projected onto the image sensors of the stereoscopic 3D camera.

Sometimes it is desirable to be able to attain a certain optical magnification of the image formed on the image sensors 29a and 29b relative to the intermediate image at the field stop 23. By way of example, in some instances the users may prefer to observe the entire field of view obtained by the endoscope. In that case the image of the field stop 23 will be projected on the image sensors in such a way that the image is inscribed inside the sensing area (see FIG. 10, left picture). The hatched area will appear black on the monitor. By way of further example, in other instances the users may prefer to fill the entire monitor with the image, which is illustrated in FIG. 10 on the right. All scenarios in between are also possible.

Figure 11:
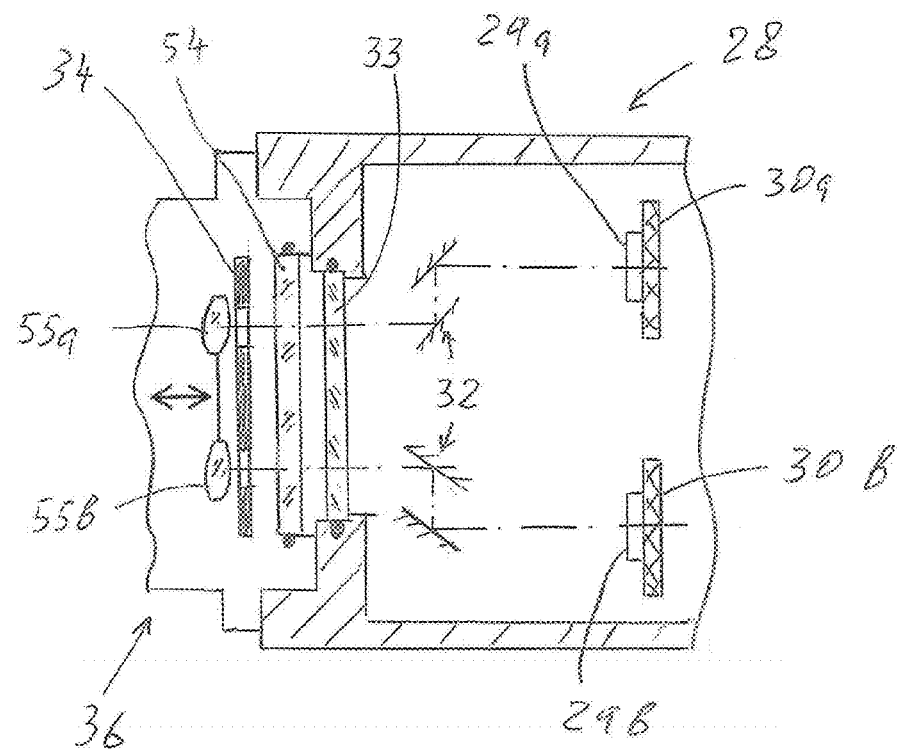
FIG. 11 is a schematic view showing another form of the present invention, wherein focusing means are included in the 3D adapter assembly, rather than in the stereoscopic 3D camera.

In conventional 2D endoscopic visualization, obtaining different magnification is achieved by either utilizing a zoom endocoupler (or a camera head with integrated zoom optics) or by using a set of fixed focal length endocouplers per user preference. In other words, the user who prefers filling the entire screen will be selecting an endocoupler with longer focus and vice versa. One drawback of the embodiment shown in FIG. 4 is that the focusing lens 35 is included in the camera head 28 assembly, which is the most expensive part of the system. In order to change magnification, a different camera head would need to be used. FIG. 11 schematically shows another embodiment of the invention overcoming this drawback. In this embodiment, the dual aperture plate 34 is included in the 3D adapter 36. Focusing lenses 55a and 55b (schematically shown as single lens elements) are disposed in 3D adapter 36 in proximity to the openings in the dual aperture plate 34. A different arrangement for channel separation is illustrated in FIG. 11 compared to FIG. 4. The channel separation elements 32 represent two sets of parallel mirror surfaces easily achieved by actual mirrors or rhomboid type prisms. FIG. 11 shows only the proximal part of the 3D adapter 36, the distal portion may be similar to the design shown in FIGS. 4, 6, 7, or to the simplified version of FIG. 9. Since the focusing lenses 55a and 55b reside within the 3D adapter 36, the image magnification is determined by a combination of the 2D endoscope 10 and the 3D adapter 36. A set of adapters with different magnifications may be used, similarly to the conventional 2D visualization using a set of 2D endocouplers.

Alternatively, lenses 55a, 56a (shown as a single lenses for illustration purpose only) may incorporate a zoom feature providing variable magnification as desired.

Thus it will be appreciated that, in order to couple a conventional 2D endoscope to a 3D camera so as to provide stereoscopic 3D visualization of a scene, an adapter must be interposed between the 2D endoscope and the 3D camera. Inasmuch as optical characteristics vary from endoscope to endoscope (depending on field stop 23, ocular focal length 24 and exit pupil diameter 26, among other things), the adapter must provide optics which are appropriate for the particular 2D endoscope being used. In one form of the invention, this is achieved by providing an adjustable 3D adapter. In another form of the invention, this is achieved by providing a kit of different 3D adapters, with an appropriate adapter being selected according to the particular 2D endoscope being used.

FURTHER MODIFICATIONS

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. An adapter for optically coupling a conventional 2D endoscope to a stereoscopic 3D camera so as to provide stereoscopic 3D visualization of an object imaged by the conventional 2D endoscope, the adapter comprising:
   a housing;
   a first mount disposed on the housing for mechanically mounting the adapter to a conventional 2D endoscope;
   a second mount disposed on the housing for mounting the housing to a stereoscopic 3D camera;
   an optical pathway disposed within the housing for receiving an image from an exit pupil of the conventional 2D endoscope and projecting the received image through an aperture plate so as to provide a 3D image of an object imaged by the conventional 2D endoscope;
   wherein the aperture plate has at least two apertures which each have a diameter equal to or less than a diameter of the image from the exit pupil;
   a first lens in the optical pathway receiving an image from the exit pupil, the first lens at a fixed distance from the exit pupil; and
   wherein the optical pathway comprises at least one optical component which is selectively movable within the housing so as to optically accommodate a range of different conventional 2D endoscopes.

2. An adapter according to claim 1 wherein the at least one optical component of the optical pathway is selectively movable within the housing so as to provide approximately the same size image on the aperture plate regardless of the particular conventional 2D endoscope which is mounted to the adapter.

3. An adapter according to claim 1 wherein the aperture plate is located on the stereoscopic 3D camera.

4. An adapter according to claim 1 wherein the aperture plate is located in the adapter.

5. An adapter according to claim 1 wherein the at least one optical component of the optical pathway is selectively movable within the housing to accommodate variations in the field stop, ocular focal length and exit pupil diameter of the particular conventional 2D endoscope mounted to the adapter.

6. An adapter according to claim 1 wherein the second mount comprises a mechanical mount on the housing for mechanically mounting the adapter to a stereoscopic 3D camera.

7. An adapter according to claim 1 wherein the second mount comprises forming the body of the adapter integral with a stereoscopic 3D camera.

8. An adapter according to claim 1 wherein the at least one optical component of the optical pathway is selectively movable within the housing so as to provide an image of adjustable size to the stereoscopic 3D camera.

9. A method for providing stereoscopic 3D visualization of an object imaged by a conventional 2D endoscope, the method comprising:
   providing an adapter for optically coupling a conventional 2D endoscope to a stereoscopic 3D camera, the adapter comprising:
      a housing;
      a first mount disposed on the housing for mechanically mounting the adapter to a conventional 2D endoscope;
      a second mount disposed on the housing for mounting the housing to a stereoscopic 3D camera;
      an optical pathway disposed within the housing for receiving an image from an exit pupil of the conventional 2D endoscope and projecting the received image through an aperture plate so as to provide a 3D image of an object imaged by the conventional 2D endoscope;
      wherein the aperture plate has at least two apertures which each have a diameter equal to or less than a diameter of the image from the exit pupil;
      a first lens in the optical pathway receiving an image from the exit pupil, the first lens at a fixed distance from the exit pupil;
      wherein the optical pathway comprises at least one optical component which is selectively movable within the housing so as to optically accommodate a range of different conventional 2D endoscopes;
   positioning the adapter between the conventional 2D endoscope and the stereoscopic 3D camera so that the adapter receives an image from the conventional 2D endoscope and projects the received image on the aperture plate; and
   moving the at least one optical component of the optical pathway of the adapter so that the image received from the conventional 2D endoscope is properly projected on the aperture plate so as to provide the 3D image of the object.

10. A method according to claim 9 wherein the at least one optical component of the optical pathway is moved so as to maintain approximately the same size image on an aperture plate regardless of the particular conventional 2D endoscope mounted to the adapter.

11. A method according to claim 9 wherein the aperture plate is located on the stereoscopic 3D camera.

12. A method according to claim 9 wherein the aperture plate is located in the adapter.

13. A method according to claim 9 wherein the at least one optical component of the optical pathway is moved so as to accommodate variations in the field stop, ocular focal length and exit pupil diameter of the particular conventional 2D endoscope mounted to the adapter.

14. A method according to claim 9 wherein the body is mounted to a stereoscopic 3D camera using a second mechanical mount on the body for mechanically mounting the adapter to a stereoscopic 3D camera.

15. A method according to claim 9 wherein the body is mounted to a stereoscopic 3D camera by forming the body integral with a stereoscopic 3D camera.

16. A method according to claim 9 wherein the at least one optical component of the optical pathway is moved so as to provide an image of adjusted size to the stereoscopic 3D camera.

17. Apparatus for providing stereoscopic 3D visualization of an object, the apparatus comprising:
   a 2D endoscope;
   a stereoscopic 3D camera; and
   an adapter for optically coupling the 2D endoscope to the stereoscopic 3D camera, the adapter comprising:
      a housing;
      a first mount disposed on the housing for mechanically mounting the adapter to the 2D endoscope;
      a second mount disposed on the housing for mounting the housing to the stereoscopic 3D camera;
      an optical pathway disposed within the housing for receiving an image from an exit pupil of the conventional 2D endoscope and projecting the received image through an aperture plate of the stereoscopic 3D camera so as to provide a 3D image of an object imaged by the conventional 2D endoscope,
   wherein the aperture plate has at least two apertures which each have a diameter equal to or less than a diameter of the image from the exit pupil;
   a first lens in the optical pathway receiving an image from the exit pupil, the first lens at a fixed distance from the exit pupil; and
   wherein the optical pathway comprises at least one optical component which is selectively movable within the housing so as to optically accommodate a range of different conventional 2D endoscopes.

18. A method for providing stereoscopic 3D visualization of an object imaged by a conventional 2D endoscope, the method comprising:
   providing apparatus for providing stereoscopic 3D visualization of an object, the apparatus comprising:
      a 2D endoscope;
      a stereoscopic 3D camera; and
      an adapter for optically coupling the 2D endoscope to the stereoscopic 3D camera, the adapter comprising:
         a housing;
         a first mount disposed on the housing for mechanically mounting the adapter to the 2D endoscope;
         a second mount disposed on the housing for mounting the housing to the stereoscopic 3D camera; and
         an optical pathway disposed within the housing for receiving an image from thean exit pupil of the conventional 2D endoscope and projecting the received image on an through an aperture plate appropriate portion of the stereoscopic 3D camera so as to provide a 3D image of an object imaged by the conventional 2D endoscope; wherein the aperture plate has at least two apertures which each have a diameter equal to or less than a diameter of the image from the exit pupil;
         a first lens in the optical pathway receiving an image from the exit pupil, the first lens at a fixed distance from the exit pupil;

wherein the optical pathway comprises at least one optical component which is selectively movable within the housing so as to optically accommodate a range of different conventional 2D endoscopes;

positioning the adapter between the conventional 2D endoscope and the stereoscopic 3D camera so that the adapter receives an image from the conventional 2D endoscope and projects the received image the aperture plate; and moving the at least one optical component of the optical pathway of the adapter so that the image received from the conventional 2D endoscope is properly projected the aperture plate as to provide the 3D image of the object.

* * * * *

UNITED STATES PATENT AND TRADEMARK OFFICE
CERTIFICATE OF CORRECTION

Page 1 of 1

PATENT NO. : 9,979,949 B2
APPLICATION NO. : 13/547510
DATED : May 22, 2018
INVENTOR(S) : Yuri Kazakevich It is certified that error appears in the above-identified patent and that said Letters Patent is hereby corrected as shown below:

In the Claims

Column 14, Line 56, please remove "the" between "from" and "an"
Column 14, Line 58, please remove "on an" between "image" and "through"
Column 14, Line 59, please remove "appropriate portion" before "of"
Column 15, Line 8, please add "through" between "image" and "the"
Column 15, Line 12, please add "through" after "projected"

Signed and Sealed this
Ninth Day of October, 2018

Andrei Iancu
*Director of the United States Patent and Trademark Office*